(12) United States Patent
Kubota et al.

(10) Patent No.: US 7,426,853 B2
(45) Date of Patent: Sep. 23, 2008

(54) APPARATUS FOR MEASURING CONCENTRATION

(75) Inventors: Yuji Kubota, Kanagawa (JP); Kei Masunishi, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 307 days.

(21) Appl. No.: 11/340,518

(22) Filed: Jan. 27, 2006

(65) Prior Publication Data

US 2006/0218995 A1  Oct. 5, 2006

(30) Foreign Application Priority Data

Mar. 30, 2005  (JP) ............... 2005-100037

(51) Int. Cl.
*G01N 29/00* (2006.01)
*G01N 29/22* (2006.01)

(52) U.S. Cl. ..................................... 73/64.53

(58) Field of Classification Search ............... 73/61.49, 73/61.79, 64.53
See application file for complete search history.

(56) References Cited

FOREIGN PATENT DOCUMENTS

| JP | 47-11515 | 10/1972 |
|---|---|---|
| JP | 61-240141 | 10/1986 |
| JP | 63-144233 | 6/1988 |
| JP | 63-313033 | 12/1988 |
| JP | 06-018394 | 1/1994 |
| JP | 9-89740 | 4/1997 |

OTHER PUBLICATIONS

Office Action issued by the Japanese Patent Office on Dec. 4, 2007, for Japanese Patent Application No. 2005-100037, and Partial English Translation of Office Action.

*Primary Examiner*—Daniel S Larkin
(74) *Attorney, Agent, or Firm*—Finnegan, Henderson, Farabow, Garrett & Dunner, L.L.P.

(57) ABSTRACT

A concentration measuring apparatus includes a vibration member; a shielding unit that limits a flowable area of a solution to be measured close to the vibration member; a vibration control unit that vibrates the vibration member at a frequency; a variation measuring unit that measures a physical variation of the vibration member vibrated; an eigenfrequency computing unit that computes an eigenfrequency of the vibration member in the solution from the frequency and the variation; and a concentration obtaining unit that obtains a concentration of the solution from the eigenfrequency and a correspondence between the eigenfrequency and the concentration of the solution.

15 Claims, 15 Drawing Sheets

| TEMPERATURE \ EIGENFREQUENCY | $f_1$ | $f_2$ | $f_3$ | $f_4$ |
|---|---|---|---|---|
| $t_1$ | $x_{11}\%$ | $x_{12}\%$ | $x_{13}\%$ | $x_{14}\%$ |
| $t_2$ | $x_{21}\%$ | $x_{22}\%$ | $x_{23}\%$ | $x_{24}\%$ |
| $t_3$ | $x_{31}\%$ | $x_{32}\%$ | $x_{33}\%$ | $x_{34}\%$ |

FIG.11
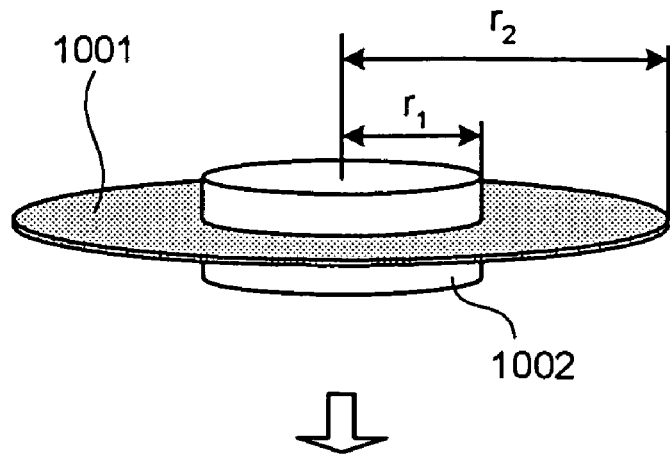
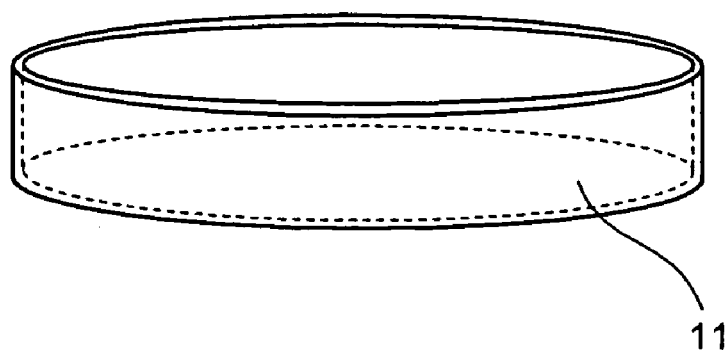
FIG.12
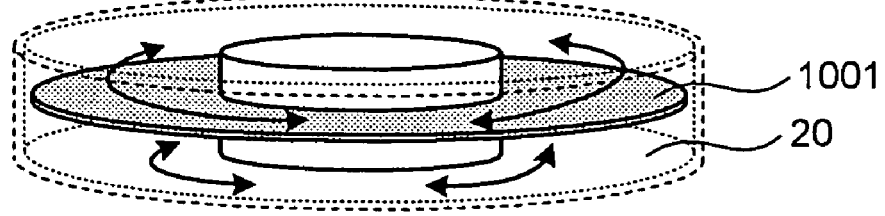

FIG.13
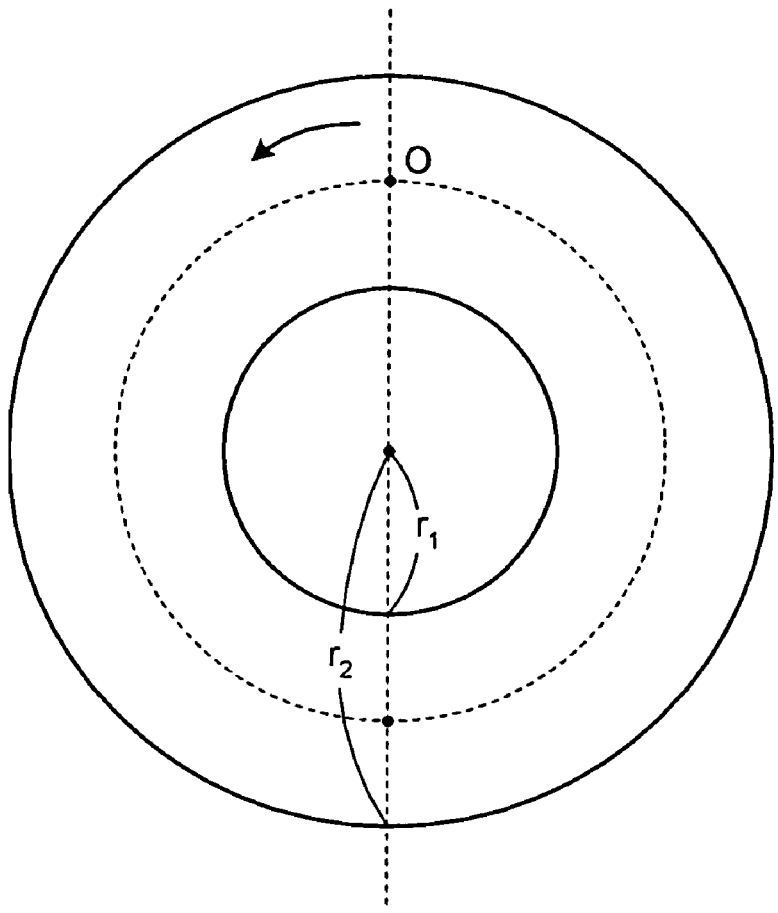
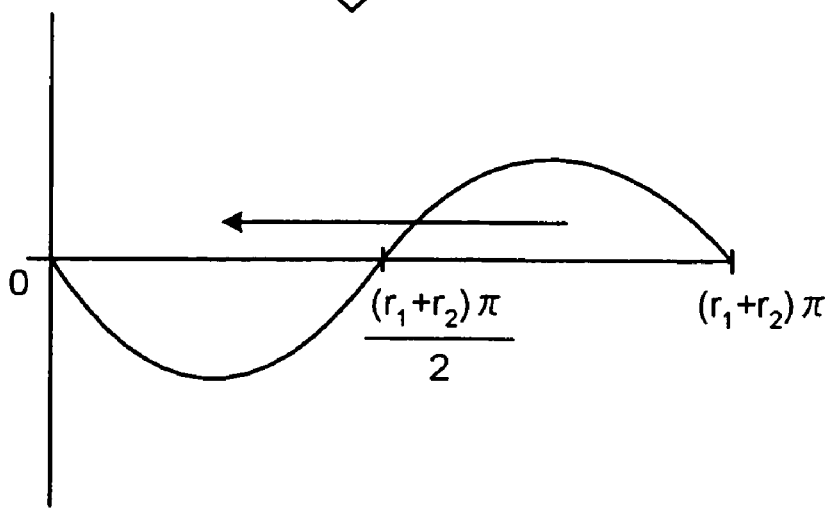

FREQUENCY IS CHANGED

APPARATUS FOR MEASURING CONCENTRATION

CROSS-REFERENCE TO RELATED APPLICATIONS

This application is based upon and claims the benefit of priority from the prior Japanese Patent Application No. 2005-100037, filed on Mar. 30, 2005; the entire contents of which are incorporated herein by reference.

BACKGROUND OF THE INVENTION

1. Field of the Invention

The present invention relates to a concentration measuring apparatus which computes a concentration of a substance to be detected based on an eigenfrequency of the substance to be detected in a mixed solution.

2. Description of the Related Art

Conventionally a number of concentration sensors utilizing a change in sound velocity according to a change in solution concentration are used. In the concentration sensor, the density can be computed by the change in sound velocity because an equation of $c=\sqrt{(K/\rho)}$ holds with respect to a sound velocity c, a density $\rho$, and volume elastic coefficient K.

More specifically, when the solution concentration is changed, both the density and volume elasticity are changed, which results in the change in sound velocity. Therefore, the solution concentration can be computed from the measured sound velocity by previously finding out a correspondence between the concentration and the sound velocity. However, generally temperature dependence of the volume elasticity is larger than that of the density. That is, because the temperature dependence of the sound velocity is larger, it is necessary that the temperature is strictly managed in measuring the change in sound velocity.

For example, in the case where the change in concentration within ±15% of a 3 wt % methanol solution at liquid temperature of 40° C. is measured by the sound velocity type concentration sensor, it is necessary the liquid temperature is managed with an accuracy not more than ±0.1° C. That is, a device for strictly managing the liquid temperature is required, which results in a problem that the concentration sensor cannot be miniaturized.

On the other hand, a technology in which the concentration is computed from the eigenfrequency of an object has been proposed as the technology in which the sound velocity dependence is smaller than that of the sound velocity type concentration sensor in computing the concentration.

For example, in the technology disclosed in Japanese Patent Application Laid-Open No. H6-18394, the concentration of the substance to be detected in the mixed solution is determined by determining the eigenfrequency of a quartz oscillator when the quartz oscillator dipped in the mixed solution is oscillated.

However, in the technology disclosed in Japanese Patent Application Laid-Open No. H6-18394, there is a problem that a flowable area such as the mixed solution which is of the detection target has an influence on accuracy of the computed concentration.

SUMMARY OF THE INVENTION

According to one aspect of the present invention, a concentration measuring apparatus includes a vibration member; a shielding unit that limits a flowable area of a solution to be measured close to the vibration member; a vibration control unit that vibrates the vibration member at a frequency; a variation measuring unit that measures a physical variation of the vibration member vibrated; an eigenfrequency computing unit that computes an eigenfrequency of the vibration member in the solution from the frequency and the variation; and a concentration obtaining unit that obtains a concentration of the solution from the eigenfrequency and a correspondence between the eigenfrequency and the concentration of the solution.

BRIEF DESCRIPTION OF THE DRAWINGS

FIG. 11 is a view for explaining structures of an elastic disc, a shielding member, and a vessel according to the second embodiment;

FIG. 12 is a view for explaining the flows of the mixed solution formed by the elastic disc, the shielding member, and the vessel according to the second embodiment;

FIG. 13 is a view for explaining the case in which the elastic disc according to the second embodiment is in the primary vibration mode;

DETAILED DESCRIPTION OF THE EMBODIMENTS

Figure 1:
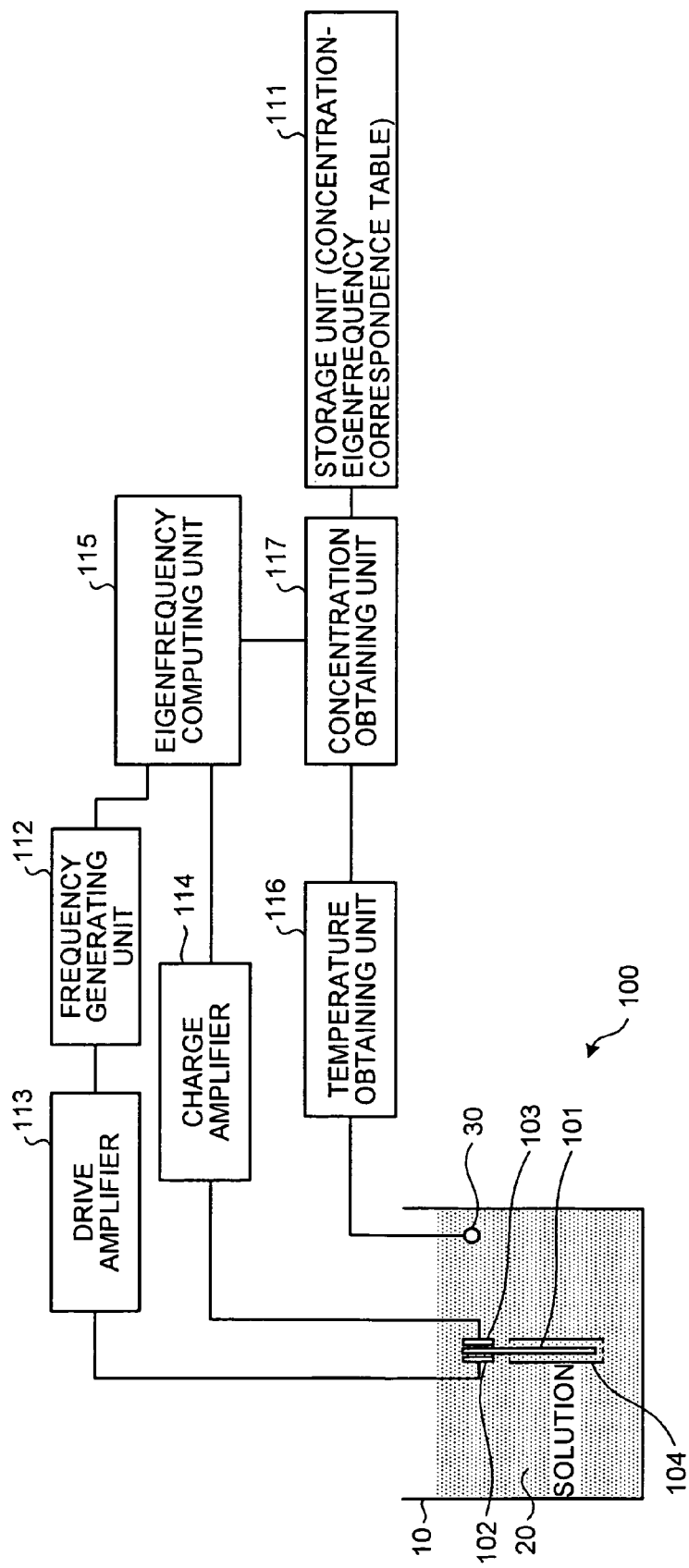
FIG. 1 is a block diagram showing a configuration of a concentration measuring apparatus according to a first embodiment.

FIG. 1 is a block diagram showing a configuration of a concentration measuring apparatus according to a first embodiment. As showing in FIG. 1, a concentration measuring apparatus 100 includes an elastic plate 101, a vibration generating actuator 102, a strain gage 103, a shielding vessel 104, a storage unit 111, a frequency generating unit 112, a drive amplifier 113, a charge amplifier 114, an eigenfrequency computing unit 115, a temperature obtaining unit 116, and a concentration obtaining unit 117. The concentration measuring apparatus 100 computes the eigenfrequency of the elastic plate 101, dipped in a mixed solution 20 in a vessel 10, to obtain the concentration of the substance to be detected in the mixed solution 20. In obtaining the concentration from the eigenfrequency, the concentration measuring apparatus 100 also obtains the concentration based on the temperature of the mixed solution 20 measured with a temperature sensor 30. Any temperature sensor may be used as the temperature sensor 30 as long as the temperature of the mixed solution 20 can be measured.

In the concentration measuring apparatus 100 of the first embodiment, it is assumed that the substance to be detected in the mixed solution 20 is previously recognized and only the concentration of the substance to be detected is unknown. That is, when the concentration measuring apparatus 100 can compute the density of the mixed solution 20, the concentration can be computed from a weight of the substance to be detected.

First a principle to measure the concentration in the concentration measuring apparatus 100 will be described. The following equation (1) holds:

$$\omega_{n,air} = \sqrt{\frac{k}{m_p}} \quad (1)$$

where $\omega_{n,air}$ is an eigenfrequency, $m_p$ is a mode mass, and k is a mode stiffness of the elastic plate 101 vibrating in an atmosphere.

The eigenfrequency $\omega_{n,air}$ in equation (1) can previously be obtained by performing the measurement in the atmosphere. When the object such as the elastic plate 101 is vibrated in the fluid of the mixed solution 20, inertia force of the fluid acts as if a mass is added to the object such as the elastic plate 101. This is referred to as an added mass effect. When equation (1) is used in consideration of the added mass effect, it is necessary that a variable of added mass $M_{fluid}$ expressing the above action is added to equation (1). Because the added mass $M_{fluid}$ becomes a value proportional to the density, the density of the mixed solution 20 can be determined when the added mass $M_{fluid}$ can be computed.

Then, in the case where the added mass $M_{fluid}$ is considered as a fluid inertia term, the eigenfrequency $\omega_{n,fluid}$ in the fluid is shown by equation (2):

$$\omega_{n,fluid} = \sqrt{\frac{k}{(m_p + M_{fluid})}} \quad (2)$$

As described above, the eigenfrequency $\omega_{n,air}$ in the atmosphere is previously obtained. Therefore, the added mass $M_{fluid}$, i.e., the density can be computed when the eigenfrequency $\omega_{n,fluid}$ in the fluid can be computed from equations (1) and (2). In the case where the density is computed, the concentration can be computed as described above.

As described above, since a correspondence holds between the eigenfrequency $\omega_{n,air}$ and the concentration, the concentration measuring apparatus 100 measures the eigenfrequency, which allows the concentration to be obtained. However, in the case of $m_p > M_{fluid}$, because the concentration change of the mixed solution 20, i.e., the eigenfrequency change according to the density change is small, detection accuracy of the concentration is not improved. Therefore, in the first embodiment, the shielding vessel 104 is provided around the elastic plate 101 in order to obtain $M_p \ll M_{fluid}$. This results in the improvement of the detection accuracy. The shielding vessel 104 will specifically be described later. Then, each component of the concentration measuring apparatus 100 will be described.

A concentration-eigenfrequency correspondence table is stored in the storage unit 111. The storage unit 111 can be formed by any one of generally used storage means such as HDD, an optical disc, and a memory card.

Figures 2, 3:
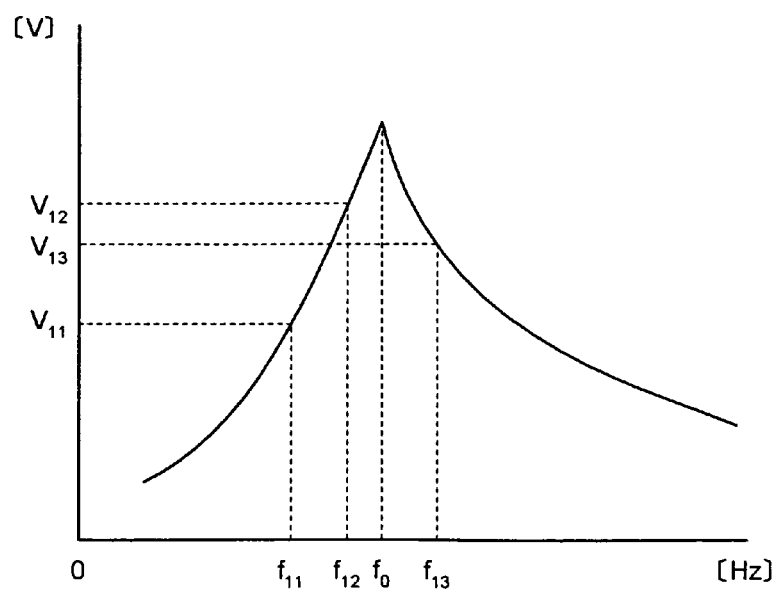
FIG. 2 is a view showing a configuration of a concentration-eigenfrequency correspondence table stored in a storage unit of the concentration measuring apparatus according to the first embodiment.
FIG. 3 is a graph showing an example of a transfer function analyzed by plural generated frequencies and corresponding displacements.

FIG. 2 is a view showing the configuration of the concentration-eigenfrequency correspondence table. As shown in FIG. 2, the concentration-eigenfrequency correspondence table includes the eigenfrequency in the fluid in one of axes and the temperature of the fluid in the other axis, and the concentrations of the substance to be detected are previously set in fields. That is, after the concentration measuring apparatus 100 computes the eigenfrequency in the fluid to obtain the temperature of the fluid, the concentration measuring apparatus 100 can refer to the concentration-eigenfrequency correspondence table to obtain the concentration of the substance to be detected. The value previously determined from experiment or characteristics of the already known substance can be used as the concentration of the substance to be detected, which is set in each field.

The frequency generating unit 112 generates the frequency, used in measuring the concentration, based on a frequency presumed to be the eigenfrequency in the mixed solution 20. The frequency generating unit 112 is also used in order to control the frequency of the elastic plate 101. The frequency presumed to be the eigenfrequency may be derived from any criterion. For example, the value of eigenfrequency held by the concentration-eigenfrequency correspondence table, the value derived based on the eigenfrequency of the elastic plate 101 in air, or the like is used for the derivation of the frequency presumed to be the eigenfrequency.

Further, in measuring the concentration of the mixed solution 20, the frequency generating unit 112 generates the plural different frequencies by switching the frequencies in each time. Thus, when the plural different frequencies are switched, the different displacement of the elastic plate 101 can be obtained in each of the different frequencies.

The drive amplifier 113 amplifies the signal indicating the frequency generated by the frequency generating unit 112, and the drive amplifier 113 outputs the amplified signal to the vibration generating actuator 102.

The vibration generating actuator 102 vibrates the elastic plate 101 at the inputted frequency, i.e., the frequency which is determined based on the frequency preseumed to be the eigenfrequency (hereinafter referred to as the frequency during measuerment)

The vibration generating actuator 102 vibrates the elastic plate 101 at the inputted frequency, i.e., the frequency which is determined based on the frequecny presumed to be the eigenfrequency (hereinafter referred to as the frequency during measurement).

The strain gage 103 is placed on the elastic plate 101, and the strain gage 103 obtains the placement of the elastic plate 101 as the voltage in the vibration by the frequency during measurement. That is, the concentration measuring apparatus 100 of the first embodiment measures the displacement as the physical variation in the vibration using the strain gage 103. The displacement measuring means is not limited to the strain gage 103, but any displacement measuring means may be used.

Because the elastic plate 101 is vibrated by the plural different numbers of vibrations during measurement, the strain gage 103 obtains the different displacement in each of the frequency during measurement. The charge amplifier 114 amplifies the voltage indicating the obtained displacement.

The eigenfrequency computing unit 115 analyzes a transfer function and computes the eigenfrequency of the elastic plate 101 from the analyzed transfer function. In the transfer function, the frequency generated by the frequency generating unit 112 is set at an input, and the displacement inputted from the charge amplifier 114 is set at an output.

FIG. 3 is a graph showing an example of the transfer function analyzed by the plural generated frequencies and the corresponding displacement. As shown in FIG. 3, the transfer function is determined from displacements $V_{11}$, $V_{12}$, and $V_{13}$ in generated frequencies $f_{11}$, $f_{12}$, and $f_{13}$, and a frequency $f_0$ which indicates the highest displacement in the transfer function can be specified as the eigenfrequency. That is, since the transfer function can be specified from the correspondence between the plural numbers of vibrations during measurement and the displacement, the eigenfrequency can be computed.

The temperature obtaining unit 116 obtains the temperature of the mixed solution 20 based on the signal inputted from the temperature sensor 30.

The concentration obtaining unit 117 obtains the concentration of the substance to be detected by referring to the eigenfrequency computed by the eigenfrequency computing unit 115, the temperature of the mixed solution 20 obtained by the temperature obtaining unit 116, and the concentration-eigenfrequency correspondence table stored in the storage unit 111.

The elastic plate 101 is formed in a so-called beam-shaped cuboid. The vibration generating actuator 102 and the strain gage 103 are placed at one end in a longitudinal direction of the cuboid. It is assumed that the eigenfrequency $\omega_{n,air}$ of the elastic plate 101 in the air is previously computed. In measuring the concentration, the elastic plate 101 is vibrated while dipped in the mixed solution 20.

The shielding vessel 104 is used as a vessel surrounding the elastic plate 101, and the shielding vessel 104 constrains the flow of the mixed solution 20 except for the longitudinal direction of the elastic plate 101.

Figure 4:
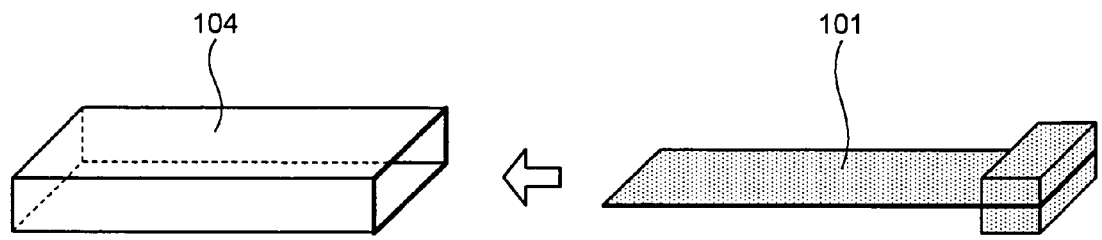
FIG. 4 is a view for explaining structures of an elastic plate and a shielding vessel according to the first embodiment.

FIG. 4 is a view for explaining structures of the elastic plate 101 and the shielding vessel 104 according to the first embodiment. As shown in FIG. 4, the shielding vessel 104 is arranged so as to surround the elastic plate 101.

In order to enhance the added mass effect, it is necessary that a flow distance of the fluid is increased in association with the vibration. Therefore, it is necessary to limit a flowable area of the fluid. In the first embodiment, the fluid flow is limited except for the longitudinal direction of the elastic plate 101. In order to limit the fluid flow only to the longitudinal direction, the elastic plate 101 is surrounded by the cylindrical shielding vessel 104 in which an opening is provided in the longitudinal direction.

Further, the fluid flow can be moved in the longitudinal direction, which allows the elastic plate 101 to be vibrated at a vibration mode having a lower order number. The vibration mode will be described later.

Figure 5:
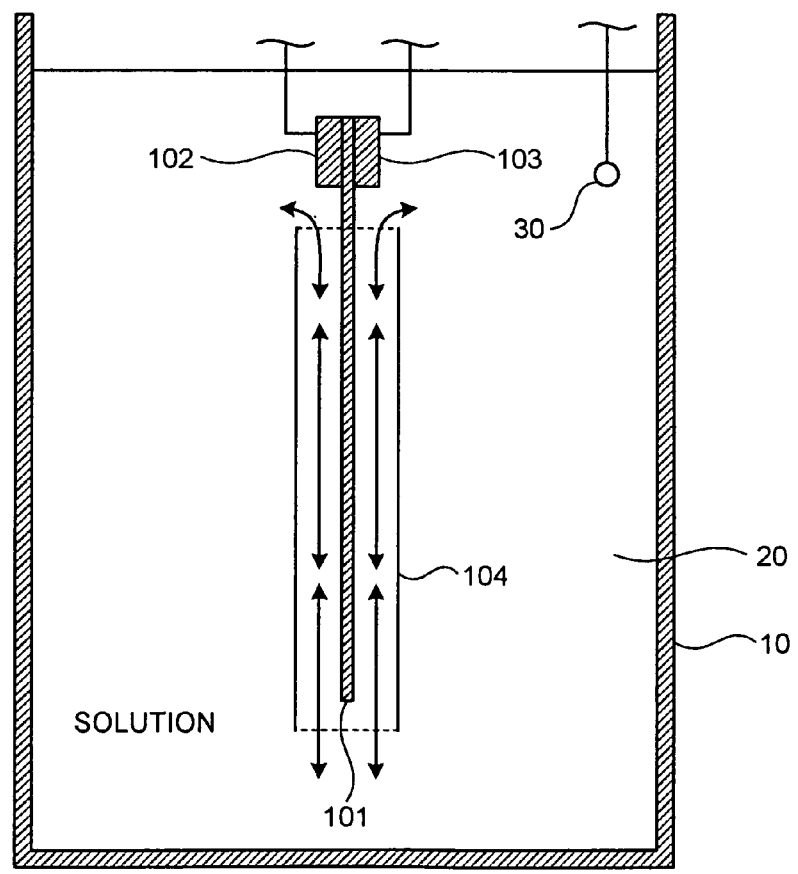
FIG. 5 is a view for explaining flows of a mixed solution close to the elastic plate constrained by an arrangement of the shielding vessel according to the first embodiment.

FIG. 5 is a view for explaining the flows of the mixed solution 20 close to the elastic plate 101 constrained by the arrangement of the shielding vessel 104. As shown in FIG. 5, the shielding vessel 104 is arranged so as to surround the elastic plate 101, which allows the flow of the mixed solution 20 to flow in the longitudinal direction while the flow of the mixed solution 20 is limited except for the longitudinal direction of the elastic plate 101. Therefore, the added mass effect is improved.

Besides the well-known fixing method, any fixing method may be used as the method of fixing the shielding vessel 104 so as to surround the elastic plate 101.

Figure 6A:
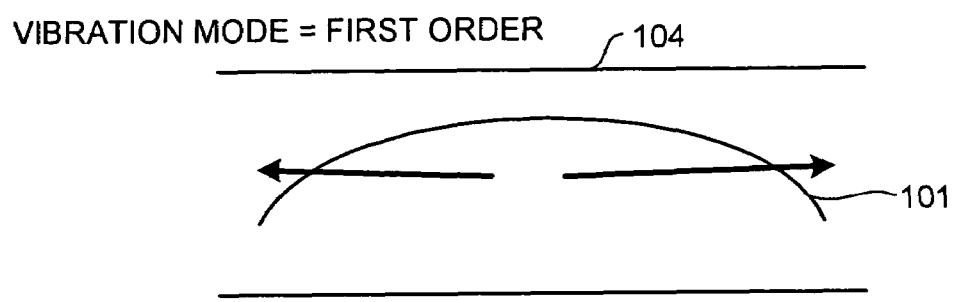
FIG. 6A is a view for explaining a flowing amount of a fluid when the elastic plate according to the first embodiment is in a primary vibration mode.
Figure 6B:
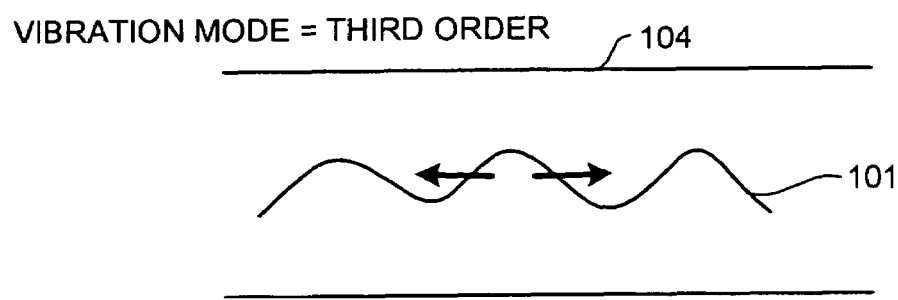
FIG. 6B is a view for explaining the flowing amount of the fluid when the elastic plate according to the first embodiment is in a third-order vibration mode.

The flow distance of the fluid depends on the order number of the vibration mode of the elastic plate 101. FIG. 6A is a view for explaining a flowing amount of a fluid when the elastic plate 101 is in a primary vibration mode. FIG. 6B is a view for explaining the flowing amount of the fluid when the elastic plate 101 is in a third-order vibration mode. In FIGS. 6A and 6B, the flow amount of the fluid is indicated by a length of an arrow. As shown in FIGS. 6A and 6B, as the order number of the vibration mode is lowered, the flow distance of the fluid becomes lengthened, so that the added mass effect is improved.

Figure 7:
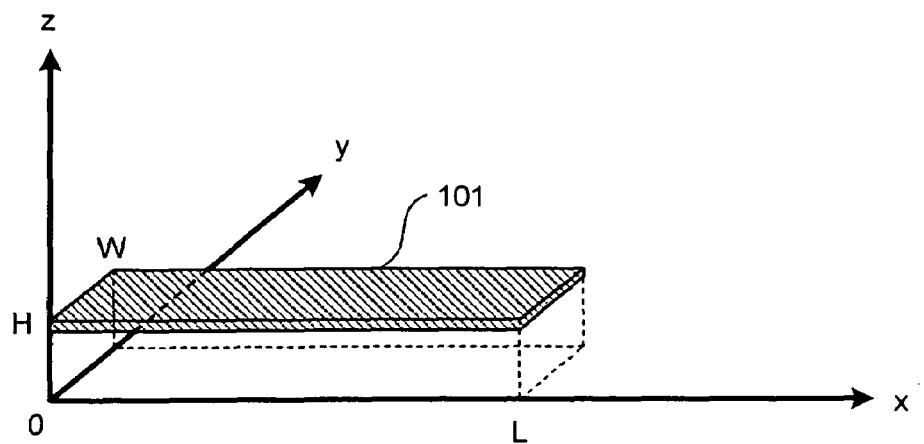
FIG. 7 is a view showing dimensions when a cross-sectional shape of a flow path becomes a rectangle by limiting the flow path with the shielding vessel and the elastic plate according to the first embodiment.

Then, an added mass effect in the case of the use of the elastic plate 101 will specifically be described. FIG. 7 is a view showing dimensions when a cross-sectional shape of a flow path becomes a rectangle by limiting the flow path with the shielding vessel 104 and the elastic plate 101. The added mass effect of the fluid by the vibration of the elastic plate 101 in the case shown in FIG. 7 will be described below. It is assumed that the fluid of mixed solution 20 is a nonviscous, incompressive potential flow. In the case of W<<L, it is assumed that the displacement in a y-direction of the elastic plate 101 is uniformed and the fluid flow in the y-direction can be neglected. On the basis of the above assumptions, a velocity potential $\phi$ of the fluid satisfies a Laplace's equation shown by equation (3):

$$\frac{\partial^2 \phi}{\partial x^2} + \frac{\partial^2 \phi}{\partial z^2} = 0 \qquad (3)$$

Boundary conditions satisfied by the velocity potential φ will be considered. At z=0, the fluid is constrained by the shielding vessel 104, so that the fluid cannot flow in a z-axis direction. Therefore, the velocity potential φ satisfies the boundary condition of equation (4):

$$\left.\frac{\partial \phi}{\partial z}\right|_{z=0} = 0 \tag{4}$$

At z=H, the fluid is in contact with the elastic plate 101. Assuming that the displacement of the elastic plate is w and a time is t, the velocity potential φ satisfies the boundary condition of equation (5):

$$\left.\frac{\partial \phi}{\partial z}\right|_{z=H} = \frac{\partial w}{\partial t} \tag{5}$$

As shown in the following equation (6), the elastic plate 101 is vibrated at an angular frequency ω while being in contact with the fluid. In equation (6), $A_m$ indicates an amplitude and m indicates the order number of the mode.

$$w = \sum_m A_m \sin\frac{m\pi x}{L} e^{j\omega t} \tag{6}$$

When the velocity potential φ is determined under the above conditions, equation (7) is derived:

$$\phi = \sum_m B_m \sin\frac{m\pi x}{L} \cosh\frac{m\pi z}{L} e^{j\omega t} \tag{7}$$

Further, a condition of orthogonality shown by equation (8) holds:

$$\int_0^L \sin\frac{m\pi x}{L} \sin\frac{n\pi x}{L} dx = 0 \quad (m \neq n) \tag{8}$$

Therefore, a coefficient $B_m$ is determined as shown in equation (9):

$$B_m = j\omega \frac{L}{m\pi \sinh\frac{m\pi H}{L}} A_m \tag{9}$$

Assuming that a pressure is p, bending stiffness of the plate is EI, the density of the elastic plate 101 is $\rho_p$, and a thickness of the elastic plate 101 is h, an oscillation equation of the elastic plate 101 can be shown by equation (10):

$$EI\frac{\partial^4 w}{\partial x^4} + \rho_p h \frac{\partial^2 w}{\partial t^2} = (p)_{z=H} \tag{10}$$

Because $(P)_{z=H}$ shown by equation (10) is the pressure acting on the elastic plate, equation (11) holds:

$$(p)_{z=H} = -\rho_{fluid} \left.\frac{\partial \phi}{\partial t}\right|_{z=H} \tag{11}$$

It is assumed that $\rho_{fluid}$ is the density of the mixed solution 20.

An equation of the frequency shown in the following equation (12) holds by equations (6) to (11).

$$\omega_{m,air}^2 - \omega^2 \left[1 + \frac{\rho_{fluid} L}{m\pi \rho_p h} \coth\frac{m\pi H}{L}\right] = 0 \tag{12}$$

At this point, as described above, $\omega_{m,air}$ is the eigenfrequency of the elastic plate 101 in the air. Equation (13) holds from $\omega_{m,air} = \sqrt{(k/m)}$:

$$\omega_{m,air}^2 = \left(\frac{m\pi}{L}\right)^4 \frac{EI}{\rho_p h} \tag{13}$$

From equation (12), an eigenfrequency ratio of the elastic plate 101 in being contact with the fluid and the elastic plate 101 in the air is expressed by equation (14):

$$\left(\frac{\omega_{m,fluid}}{\omega_{m,air}}\right)^2 = \frac{1}{1+\gamma_m} \tag{14}$$

In $\gamma_m$ of equation (14), equation (15) holds:

$$\gamma_m = \frac{\rho_{fluid} L}{m\pi \rho_p h} \coth\frac{m\pi H}{L} \tag{15}$$

$\gamma_m = M_{fluid}/m_p$ holds from equations (1) and (2).

Therefore, as the value of $\gamma_m$ shown by equation (15) is increased, the measurement accuracy of the concentration is improved.

Figure 8:
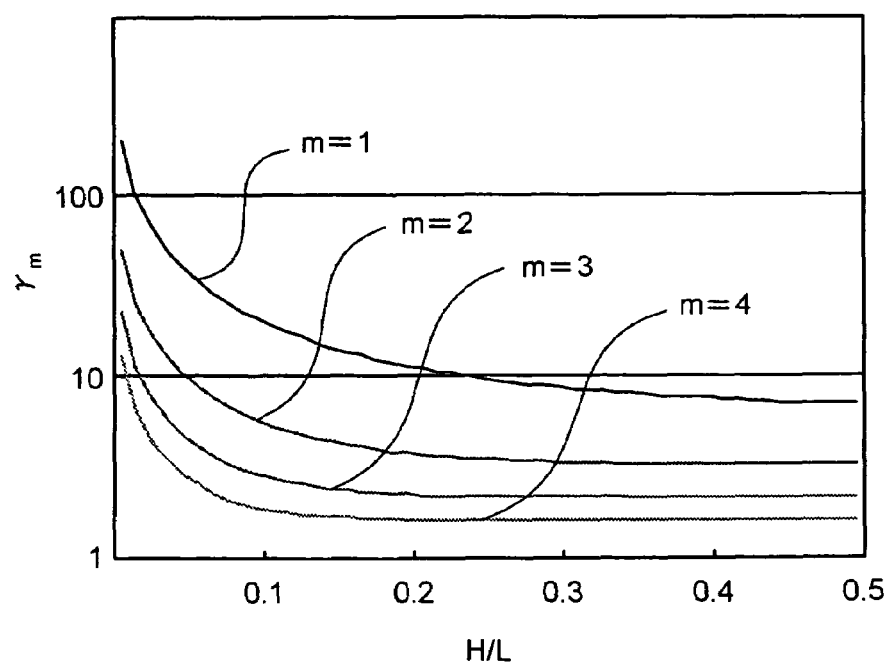
FIG. 8 is a graph showing a change in value of $\gamma m$ when a value of H/L is changed in each order of the vibration mode in the concentration measuring apparatus according to the first embodiment.

FIG. 8 is a graph showing the change in value of γm when the value of H/L is changed in each order number of the vibration mode. When the graph is determined, it is assumed that $\rho_p/\rho_{fluid}$=2.5 and L/h=50. As shown in the graph, the value of H/L is decreased and the vibration mode having the lower order number is used, which allows the value of $\gamma_m$ can be increased, namely, the measurement accuracy of the concentration can be improved. It is thought that the value of H/L is decreased by bringing the shielding vessel 104 close to the elastic plate 101, by using the elastic plate 101 which is long in the longitudinal direction, or the like.

That is, the flow distance of the fluid is increased to improve the added mass effect by using the vibration mode having the lower order number, by bringing the shielding vessel 104 close to the elastic plate 101, or by using the elastic plate 101 which is long in the longitudinal direction. Therefore, the measurement accuracy of the concentration is improved.

Figure 9:
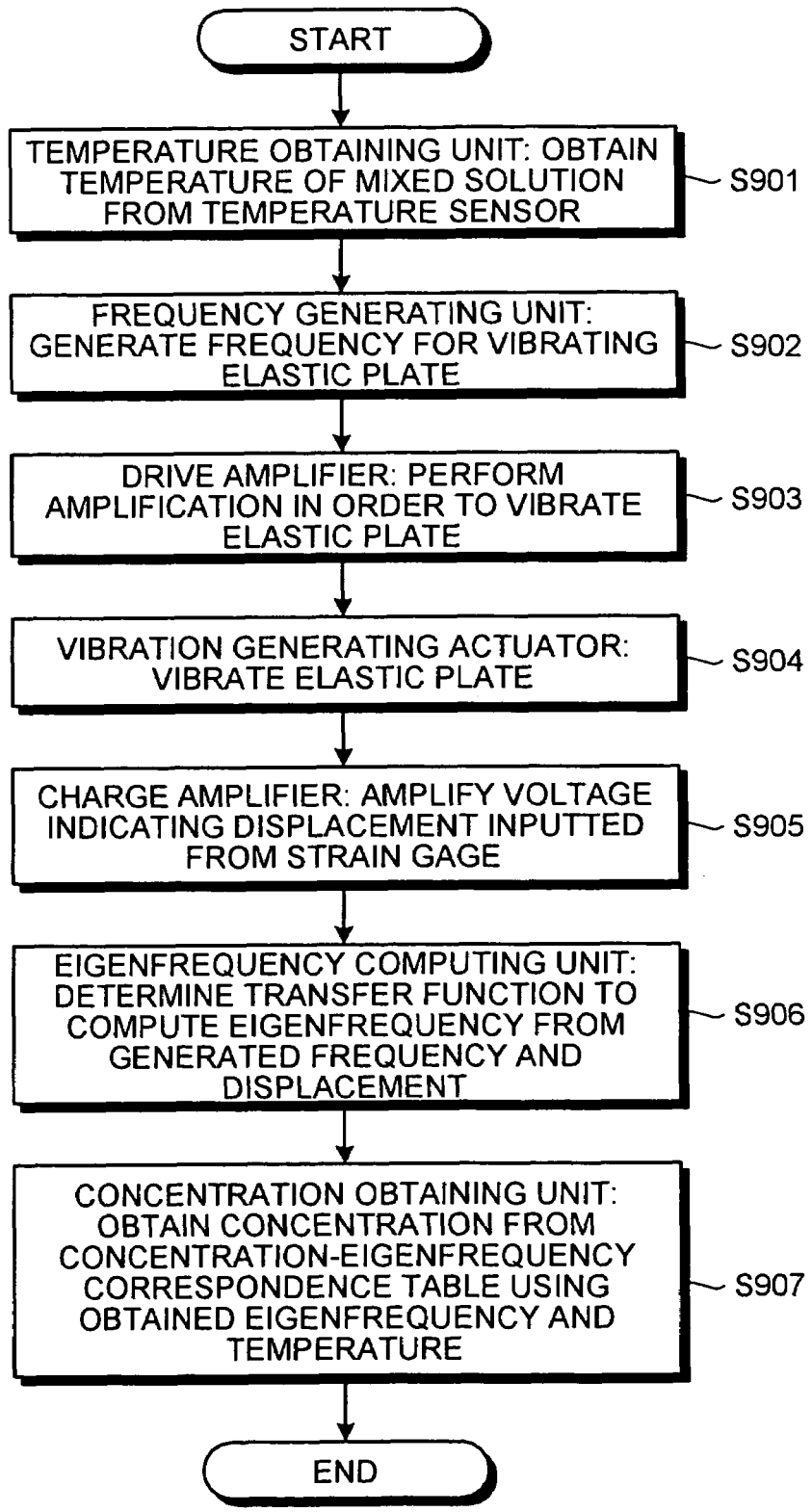
FIG. 9 is a flowchart showing a procedure from obtaining a temperature of the mixed solution until obtaining a concentration of the mixed solution in the concentration measuring apparatus according to the first embodiment.

In the concentration measuring apparatus 100 according to the first embodiment, the processes from obtaining the temperature of the mixed solution 20 to obtaining the concentration of the mixed solution 20 will be described below. FIG. 9 is a flowchart showing a procedure of the above process in the concentration measuring apparatus 100 according to the first embodiment. In measuring the concentration, the temperature sensor 30 and the elastic plate 101 surrounded by the shielding vessel 104 are previously dipped in the mixed solution 20 in the vessel 10.

The temperature obtaining unit 116 obtains the temperature of the mixed solution 20 from the temperature sensor 30 (Step S901).

The frequency generating unit 112 generates the frequency vibrating the elastic plate 101 (Step S902). It is assumed that the plural frequencies, determined based on the frequency presumed to be the eigenfrequency in the mixed solution 20, are switched in each time. Then, the drive amplifier 113 amplifies the frequency generated in Step S902 in order to vibrate the elastic plate 101 (Step S903). The vibration generating actuator 102 vibrates the elastic plate 101 with the signal amplified in Step S903 (Step S904).

The charge amplifier 114 amplifies the voltage indicating the displacement which is inputted from the strain gage 103 placed on the elastic plate 101 (Step S905).

The eigenfrequency computing unit 115 determines the transfer function from the generated frequency and the inputted displacement, and the eigenfrequency computing unit 115 computes the frequency having the largest displacement in the transfer function as the eigenfrequency (Step S906).

The concentration obtaining unit 117 obtains the concentration of the mixed solution 20 from the concentration-eigenfrequency correspondence table stored in the storage unit 111 by using the eigenfrequency computed in Step S906 and the temperature obtained in Step S901 (Step S907).

The concentration of the mixed solution 20 can be obtained with high accuracy through the above procedure. However, the above procedure is illustrated as an example of the procedure from obtaining the temperature of the mixed solution 20 to obtaining the concentration of the mixed solution 20 in the first embodiment, and the first embodiment is not limited to the above procedure. For example, it is possible that obtaining the temperature is performed after computing the eigenfrequency.

In the first embodiment, the physical variation which is of the measuring subject is not limited to the displacement. For example, velocity or acceleration may be computed as the physical variation. Because the eigenfrequency can be computed from the variation of the velocity or acceleration, the concentration can be computed. In the case where the velocity or acceleration is used as the physical variation to perform the measurement, a velocity sensor or an acceleration sensor is used instead of the strain gage 103.

Since the concentration measuring apparatus 100 according to the first embodiment limits the flowable area of the solution with the shielding unit, the flow distance of the fluid is increased to improve the added mass effect, which allows the measurement accuracy of the concentration to be improved. Further, in the concentration measuring apparatus 100 according to the first embodiment, since the temperature dependence is decreased, cost necessary for the temperature control can be reduced while decreasing a load of managing the temperature of the mixed solution 20. Further, since the component necessary for the temperature control can be neglected, the miniaturization can be achieved.

The flow distance of the mixed solution 20 is lengthened to enhance the added mass effect by limiting the flow area of the mixed solution 20 with the shielding vessel 104 during the vibration of the elastic plate 101. Therefore, the accuracy of the measured concentration is improved.

With respect to the vibration mode, the added mass effect is enhanced by the vibration having the lower order number such as the first order, which improves the accuracy of the measured concentration. As the distance between the surfaces of the elastic plate 101 and the shielding vessel 104 is shortened, or as the length in the longitudinal direction of the elastic plate 101 is lengthened, the accuracy of the concentration is improved.

In order to enhance the added mass effect of the fluid to improve the measuring accuracy of the concentration, it is necessary to increase the flow distance of the fluid of the mixed solution 20. However, the flow-distance increasing method is not limited to the method of surrounding the beam-shaped elastic plate 101 with the shielding vessel 104 as shown in the first embodiment. Therefore, the case in which the vibration member vibrated is formed in a ring-shaped elastic disc will be described in a second embodiment.

Figure 10:
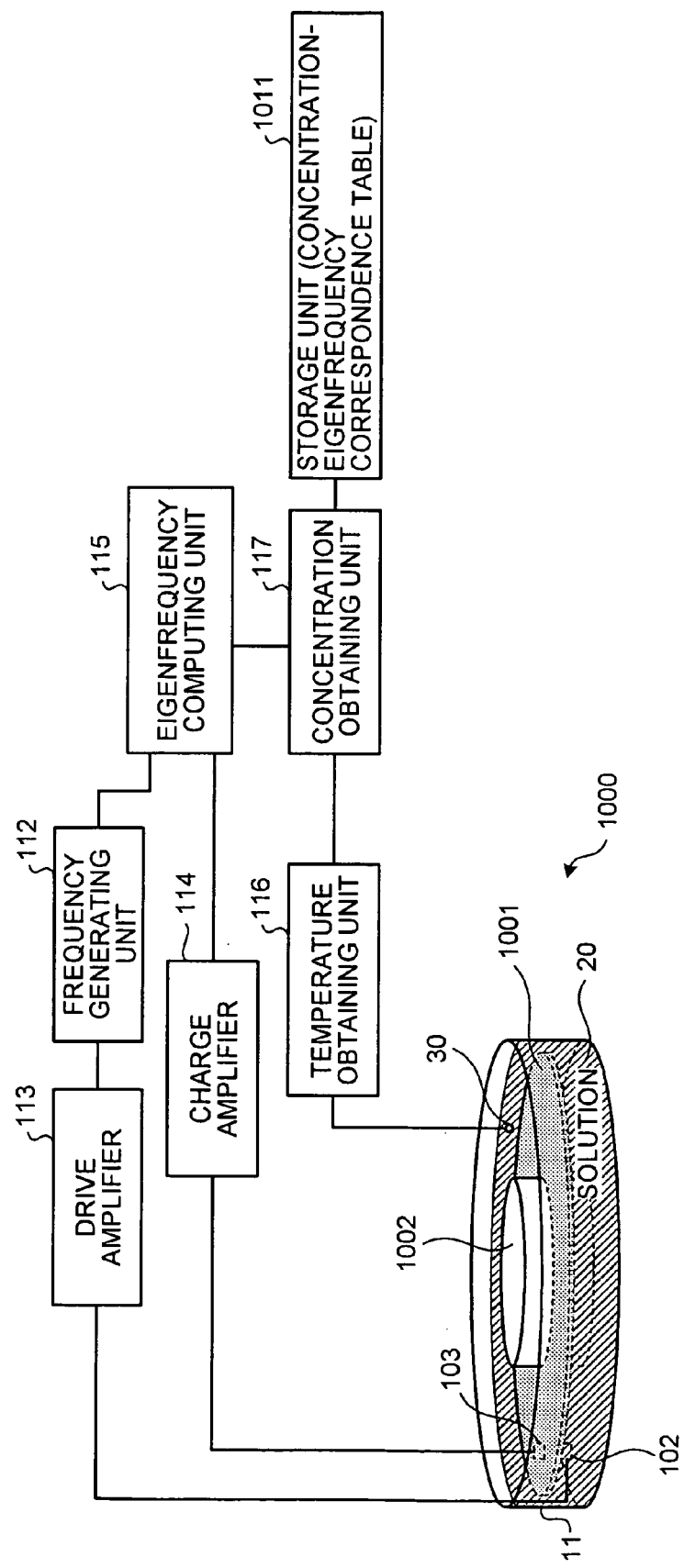
FIG. 10 is a block diagram showing a configuration of a concentration measuring apparatus according to a second embodiment.

FIG. 10 is a block diagram showing a configuration of a concentration measuring apparatus 1000 according to a second embodiment. The concentration measuring apparatus 1000 according to the second embodiment differs from the concentration measuring apparatus 100 according to the first embodiment in that the elastic plate 101 is changed to a ring-shaped elastic disc 1001, the shielding vessel 104 is changed to a shielding member 1002 limiting the flow distance of the fluid of the mixed solution 20 and a vessel 11, and the storage unit 111 is changed to the storage unit 1011 in which the information different from the storage unit 111 is stored. In the second embodiment, the same components as the first embodiment are indicated by the same numerals to neglect the description.

A concentration-eigenfrequency correspondence table is stored in the storage unit 1011. As shown in FIG. 2, the concentration-eigenfrequency correspondence table includes the eigenfrequency in the fluid in one of axes and the temperature of the fluid in the other axis, and the concentrations of the substance to be detected are previously set in fields. However, the concentration-eigenfrequency correspondence table stored in the storage unit 1011 of the second embodiment differs from the concentration-eigenfrequency correspondence table of the first embodiment in that the information for specifying the eigenfrequency of the elastic disc 1001 is stored. Therefore, the concentration can be obtained from the eigenfrequency of the elastic disc 1001.

Any member may be used as the shielding member 1002 as long as the member limits the flow toward the inner circle side of the fluid such as the mixed solution 20 in the radial direction. In the second embodiment, it is assumed that the shielding member 1002 is formed in a circular cylinder.

Similarly to the elastic plate 101 of the first embodiment, the vibration generating actuator 102 and the strain gage 103 are placed on the elastic disc 1001. Therefore, the elastic disc 1001 can be vibrated to measure the displacement.

FIG. 11 is a view for explaining the structures of the elastic disc 1001, the shielding member 1002, and the vessel 11. As shown in FIG. 11, the elastic disc 1001 and the shielding member 1002 are combined. The vessel 11 is formed in the cylindrical shape as shown in FIG. 11, and the mixed solution 20 is stored inside the vessel 11. The shielding member 1002 is formed in the circular cylinder, and a radius of the shielding member 1002 is set at $r_1$. In the elastic disc 1001, an inner radius is set at $r_1$, and an outer radius is set at $r_2$. Therefore, an inner circle of the elastic disc 1001 having the inner radius of $r_1$ can be inserted into the shielding member 1002. Thus, the flow toward the inner circle side of the fluid of the mixed solution 20 which is in contact with the elastic disc 1001 is limited in the radial direction of the elastic disc 1001 by combining the elastic disc 1001 and the shielding member 1002. The second embodiment is described on the assumption that the radius of the shielding member 1002 is equal to the inner radius of the elastic disc 1001. However, in the actual concentration measuring apparatus 1000, a gap exists between the outer surface of the shielding member 1002 and the inner radius of the elastic disc 1001 such that the elastic disc 1001 can be vibrated. That is, the radius of the shielding member 1002 is slightly smaller than $r_1$, and the inner radius of the elastic disc 1001 is slightly larger than $r_1$. The gap is set from the viewpoints of a machining tolerance, an assembly tolerance, and the gap necessary for the vibration of the elastic disc 1001.

As shown in FIG. 11, the combined elastic disc 1001 and shielding member 1002 are placed in the vessel 11. Therefore, the flow toward the outer circle side in the radial direction is limited in the fluid such as the mixed solution 20 in the vessel 11.

FIG. 12 is a view for explaining the flows of the mixed solution 20 formed by the elastic disc 1001, the shielding member 1002, and the vessel 11. As shown in FIG. 12, the flows toward the inner circle side and the outer circle side in the radial direction are limited in the mixed solution 20, and the mixed solution 20 can flow in a circumferential direction.

The elastic disc 1001 is vibrated by the vibration generating actuator 102 at the frequency generated by the frequency generating unit 112. The concentration is obtained based on the added mass effect generated by the vibration. Then, the order number of the vibration mode and the flow distance of the fluid in the second embodiment will be described.

FIG. 13 is a view for explaining the case in which the elastic disc 1001 is in the primary vibration mode. As shown in FIG. 13, when the vibration mode is in the first order, the amplitude which makes a round of the shielding member 1002 from a point O is shown in the lower graph. In this case, the flow distance of the fluid is shown by the length of the arrow in the lower graph. Similarly to the first embodiment, as the order number of the vibration mode is increased, the flow distance becomes shorter.

Figure 14:
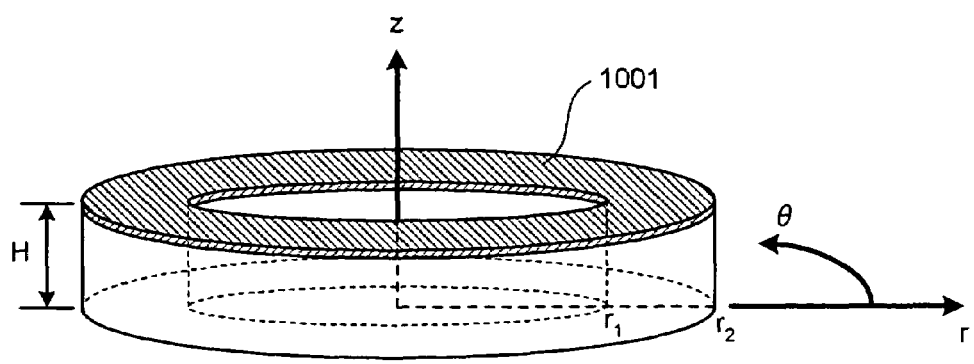
FIG. 14 is a view showing the dimensions when a top surface is formed by an elastic disc on the condition that the flow path is limited by the elastic disc, the shielding member, and the vessel according to the second embodiment.

Then, the added mass effect in the case of the use of the elastic disc 1001 will specifically be described. FIG. 14 is a view showing the dimensions when a top surface is formed by the elastic disc 1001 on the condition that the flow path is limited by the elastic disc 1001, the shielding member 1002, and the vessel 11. The added mass effect of the fluid by the vibration of the elastic disc 1001 in the case shown in FIG. 14 will be described. As with the first embodiment, it is assumed that the fluid of mixed solution 20 is the nonviscous, incompressive potential flow. In the case of $r_2-r_1 \ll r_2$, it is assumed that the displacement in the radial direction of the elastic plate 1001 is uniformed and the fluid flow in the radial direction can be neglected. In this case, the method of computing the value of γm in equation (14) is not particularly described. However, the following equation (16) can be determined from a reference document (Kubota and Suzuki, "The added mass effect acting on a vibration disc in a fluid" Transaction of the Japan Society of Mechanical Engineers C, 50-449(1984), P243-248).

$$\gamma_m = \frac{\rho_{fluid} r_0}{m \rho_p h} \coth \frac{mH}{r_0} \quad (16)$$

where $r_0$ is an average radius of the elastic disc 1001, and $r_0$ can be determined from $r_0=(r_1+r_2)/2$.

Naturally, as with the first embodiment, the following relationship holds: $\gamma m = M_{fluid}/m_p$. Accordingly, as the value of $\gamma_m$ shown by equation (16) is increased, the measuring accuracy of the concentration is improved.

Figure 15:
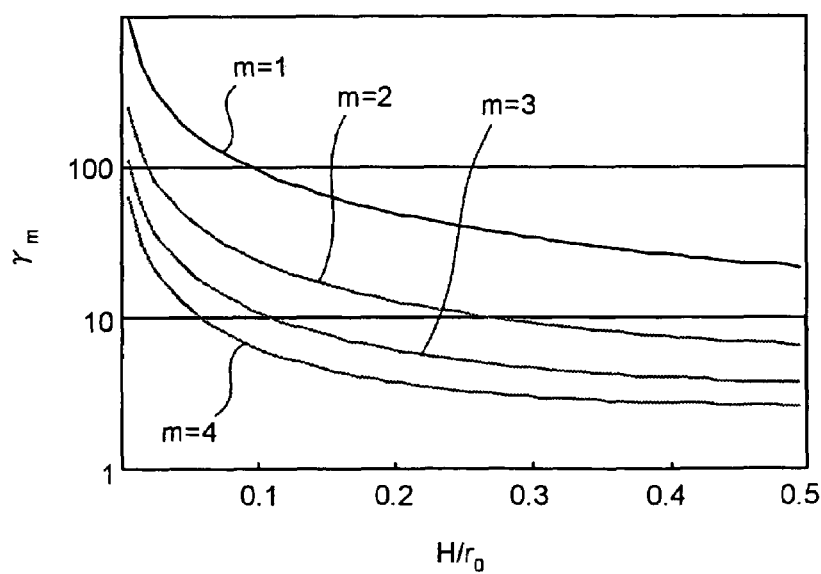
FIG. 15 is a graph showing the change in value of $\gamma m$ when a value of $H/r_0$ is changed in each order of the vibration mode.

FIG. 15 is a graph showing the change in value of $\gamma_m$ when the value of $H/r_0$ is changed in each order number of the vibration mode. When the graph is determined, it is assumed that $\rho_p/\rho_{fluid}=2.5$ and $r_0/h=50$. As shown in the graph, the value of $r_0/L$ is decreased and the vibration mode having the lower order number is used, which allows the value of $\gamma_m$ can be increased, namely, the measurement accuracy of the concentration can be improved. It is thought that the value of $r_0/L$ is decreased by bringing the vessel 11 close to the elastic disc 1001, by using the elastic disc 1001 having the large average radius $r_0$, or the like.

As with the first embodiment, the flow distance of the fluid is increased to improve the added mass effect by using the vibration mode having the lower order number, by bringing the vessel 11 close to the elastic disc 1001, or by using the elastic disc 1001 having the large average radius $r_0$. Therefore, the measurement accuracy of the concentration is improved.

The procedure performed in the concentration measuring apparatus 1000 according to the second embodiment is similar to the procedure shown in the first embodiment, so that the description will be neglected.

The second embodiment has the following advantage similar to the first embodiment. That is, the flow direction of the fluid of the mixed solution 20 becomes the circumferential direction by using the elastic disc 1001, which allows the flow distance to be increased compared with the linear flow direction in the case of the use of the vessel having the same dimensions. Accordingly, the measurement accuracy of the concentration is further improved.

In the second embodiment, the shape of the elastic disc 1001 is not particularly limited. However, in order to limit the fluid flow in the radial direction to improve the measurement accuracy of the concentration, it is desirable that a ratio of the inner radius and the outer radius is set to at least ⅓.

In the second embodiment, the shape of the vessel 11 is not particularly limited. However, in order to limit the fluid flow in the direction perpendicular to the elastic disc 1001 to improve the measurement accuracy of the concentration, it is desirable that at least one of the upper and lower ends of the vessel 11 is closed. That is, when the elastic disc 1001 is vibrated with respect to the fluid, the fluid flow in the amplitude direction is limited by closing at least one of the upper and lower ends of the vessel 11, so that the flow distance of the fluid is increased to further improve the added mass effect. In the second embodiment, since the elastic disc 1001 is placed inside the vessel 11, the same effect as the closed lower end is obtained.

In the second embodiment, the elastic disc 1001 is used as the vibration member, and vessel 11 is formed in the circular container into which the elastic disc 1001 is fitted. However, the vessel 11 is not limited to the circle. For example, as with the first embodiment, the vessel 11 is not particularly limited, the shielding vessel and the vibration member which are dipped in the mixed solution may be formed in the circle. In order to prevent the mixed solution from remaining in the shielding vessel, the pump action may be generated by the fluid flow. Therefore, a third embodiment will be described below. In the third embodiment, the shielding vessel and the vibration member are formed in the circle, and the pump action is generated using the flow of the mixed solution by the excited progressive wave.

Figure 16:
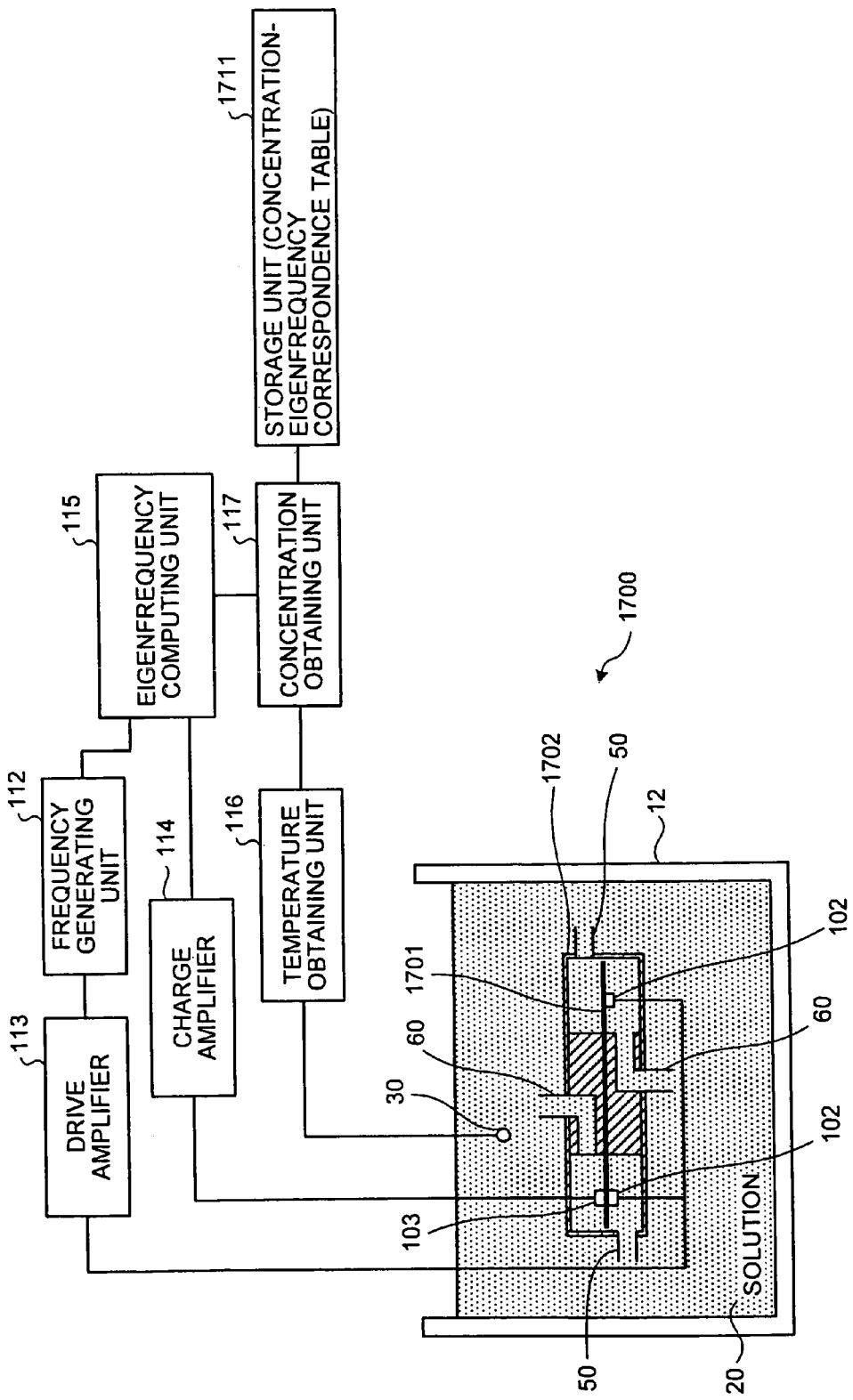
FIG. 16 is a block diagram showing a configuration of a concentration measuring apparatus according to a third embodiment.

FIG. 16 is a block diagram showing a configuration of a concentration measuring apparatus 1700 according to the third embodiment. The concentration measuring apparatus 1700 according to the third embodiment differs from the concentration measuring apparatus 1000 according to the second embodiment in that a vessel 12 is filled with the mixed solution 20, the elastic disc 1001 is changed to a elastic disc 1701 having different dimensions from the elastic disc 1001, a shielding vessel 1702 is added, the plural vibration generating actuators 102 are placed, and the storage unit 1011 is changed to a storage unit 1711 in which the information different from the storage unit 1011 is stored. In the third embodiment, the same components as the second embodiment are indicated by the same numerals to neglect the description.

A concentration-eigenfrequency correspondence table is stored in the storage unit 1711. As shown in FIG. 2, the concentration-eigenfrequency correspondence table includes the eigenfrequency in the fluid in one of axes and the temperature of the fluid in the other axis, and the concentrations of the substance to be detected are previously set in fields. However, the concentration-eigenfrequency correspondence table stored in the storage unit 1711 of the third embodiment differs from the concentration-eigenfrequency correspondence table of the second embodiment in that the information for specifying the eigenfrequency of the elastic disc 1701 used in the third embodiment is stored. Therefore, the concentration can be obtained from the eigenfrequency of the elastic disc 1701.

The plural vibration generating actuators 102 and the one strain gage 103 are placed on the elastic disc 1701. The plural vibration generating actuators 102 generate the vibration, which selectively excites only the progressive wave to generate the fluid flow on the predetermined conditions.

Then, a mounting position of the vibration generating actuator 102 for exciting the progressive wave will be described. In the following description, as with the second embodiment shown in FIG. 14, it is assumed that the inner radius of the elastic disc 1701 is $r_1$, the outer radius of the elastic disc 1701 is $r_2$, and the distance between the elastic disc 1701 and the shielding vessel 1702 is H. The vibration is generated by mounting the one vibration generating actuator 102 at the position of $\theta=0$.

When the vibration is generated at an intrinsic angular frequency $\omega_m$ having the number of nodal diameters m by the mounted vibration generating actuator 102, a standing wave shown by the following equation (17) is excited:

$$w_{1,m} = A_m \cos m\theta \sin \omega_m t \tag{17}$$

The displacement generated by the vibration generating actuator 102 is set at $w_{1,m}$, and the amplitude generated by the intrinsic angular frequency $\omega_m$ is set at $A_m$.

Equation (17) is rewritten by equation (18):

$$w_{1,m} = \frac{A_m}{2}[\sin(m\theta + \omega_m t) - \sin(m\theta - \omega_m t)] \tag{18}$$

In equation (18), the first term in the square bracket on the right-hand side indicates a regressive wave having phase velocity of $\theta=-\omega_m t/m$, and the second term indicates the progressive wave having the phase velocity of $\theta=\omega_m t/m$.

The following equation (19) shows the case, in which another vibration generating actuator 102 is mounted at the position of $\theta=\theta_2$ and a phase difference $\psi$ is further added to the same amplitude and the same angular frequency $\omega_m$ as equation (17) to generate the vibration.

$$w_{2,m} = A_m \cos m(\theta - \theta_2)\sin(\omega_m t - \psi) \tag{19}$$

$$= \frac{A_m}{2}[\sin\{(m\theta + \omega_m t) - (m\theta_2 + \psi)\} - \sin\{(m\theta - \omega_m t) - (m\theta_2 + \psi)\}]$$

The displacement generated by another vibration generating actuator 102 is set at $w_{2,m}$.

In consideration of the case in which the vibration shown by equation (18) and the vibration shown by equation (19) are simultaneously excited, the vibration of the elastic disc 1701 is shown by equation (20):

$$w_{1,m} + w_{2,m} = \frac{A_m}{2}\left[\sin\left\{(m\theta + \omega_m t) - \frac{m\theta_2 + \psi}{2}\right\}\cos\frac{m\theta_2 + \psi}{2} - \sin\left\{(m\theta + \omega_m t) - \frac{m\theta_2 - \psi}{2}\right\}\cos\frac{m\theta_2 - \psi}{2}\right] \tag{20}$$

The conditions, in which the amplitude of the regressive wave of the first term in the square bracket on the right-hand side of equation (20) becomes zero and the amplitude of the progressive wave of the second term becomes the maximum, are shown by equations (21) and (22):

$$\frac{m\theta_2 + \psi}{2} = \left(\frac{1}{2} + i\right)\pi \tag{21}$$

$$\frac{m\theta_2 + \psi}{2} = k\pi \tag{22}$$

In equations (21) and (22), i and k are an arbitrary integer. Accordingly, the condition that only the progressive wave is selectively excited by generating the vibration at two points becomes equations (23) and (24):

$$\theta_2 = \left(\frac{1}{2} + i + k\right)\frac{\pi}{m} \tag{23}$$

$$\psi = \left(\frac{1}{2} + i - k\right)\pi \tag{24}$$

It is assumed that another vibration generating actuator 102 is mounted such that the conditions of equations (23) and (24) are satisfied, which enables only the progressive wave to be excited.

Figure 17:
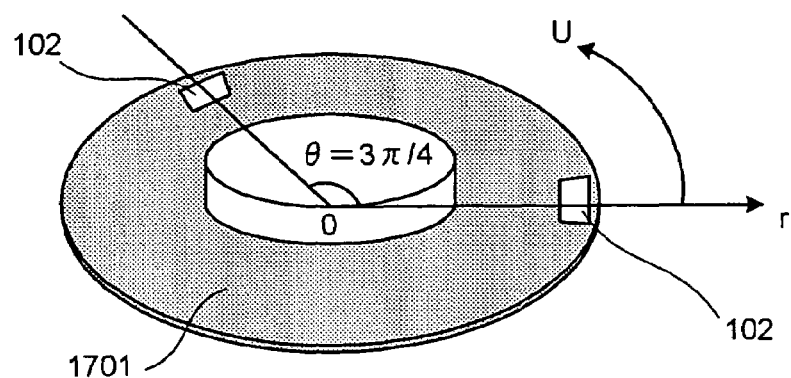
FIG. 17 is a view for explaining an example of an arrangement in which vibration generating actuators are mounted onto the elastic disc such that the mixed solution does not remain in the concentration measuring apparatus according to the third embodiment.

FIG. 17 is a view for explaining an example of the arrangement in which the vibration generating actuators 102 is mounted onto the elastic disc 1701 such that the mixed solution 20 does not remain. In the third embodiment shown in FIG. 17, it is assumed that the progressive wave having the two nodal diameters performs the excitation. One of the vibration generating actuators 102 generates the vibration at the position of $\theta=0$ with sin $\omega t$, and the other vibration generating actuator 102 generates the vibration at the position of $\theta=3\pi/4$ with sin $(\omega t-\pi/2)$. That is, the vibrations are generated on the conditions that can be derived in the case of m=2, i=0, and k=1 in equations (23) and (24). Therefore, only the progressive wave is selectively excited, and the fluid of the mixed solution 20 flows.

Returning to FIG. 16, the shielding vessel 1702 is formed in an enclosed structure in which the fluid flow is limited in the radial direction, i.e., toward the inner circle side and the outer circle side and the flow is limited in the direction perpendicular to the elastic disc 1701. In the enclosed structure of the shielding vessel 1702, an opening 60 which becomes the flow path of the fluid is provided on the inner circle side, and an opening 50 which becomes the flow path of the fluid is provided on the outer circle side. The shielding vessel 1702 has the above configuration to generate the fluid flows of the mixed solution 20, which generates the pump action.

Figure 18:
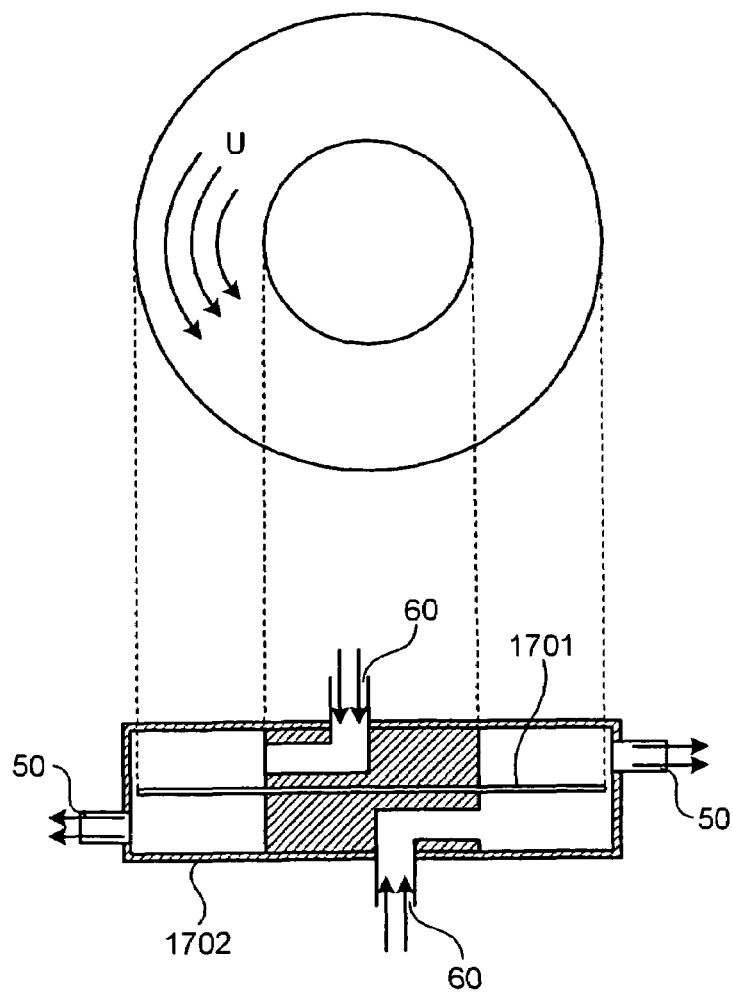
FIG. 18 is a view for explaining a pump action generated by utilizing the fluid flows of the mixed solution in the concentration measuring apparatus according to the third embodiment.

FIG. 18 is a view for explaining the pump action generated by utilizing the fluid flows of the mixed solution 20. As shown in FIG. 18, a centrifugal force is generated in the mixed solution 20 by a fluid flow U. The fluid flow U is generated in the circumferential direction by the progressive wave. Since the opening 50 which becomes the flow path of the fluid is provided on the outer circle side of the shielding vessel 1702, the fluid of the mixed solution 20 flows out from the opening 50 to the outside. Since the fluid flows out from the opening 50 to the outside, the fluid of the mixed solution 20 flows into from the opening 60 provided on the inner circle side of the shielding vessel 1702.

That is, the pump action in which the flow-out and flow-in of the fluid are always performed in generating the vibration is operated, so that the mixed solution 20 is prevented from remaining.

The procedure performed in the concentration measuring apparatus 1700 according to the third embodiment is similar to the procedure shown in the first embodiment, so that the description will be neglected.

In the third embodiment, when the pump action is operated to the mixed solution 20, the concentration of the mixed solution 20 becomes uniform, which improves the measuring accuracy of the concentration.

In the third embodiment, the plural vibration generating actuators 102 are placed on the elastic disc 1701, and the progressive wave is excited to generate the pump action. However, the component for generating the pump action is not limited to the elastic disc 1701. For example, the plural vibration generating actuators mounted on the elastic plate shown in the first embodiment, and only the progressive wave is excited to generate the flow, and the fluid may be prevented from remaining.

Further, the invention is not limited to the above embodiments. The various modifications can be made as follows.

In the embodiments, the transfer function is analyzed to compute the eigenfrequency based on the plural generated frequencies and the plural displacements corresponding to the frequencies. However, the method of computing the eigenfrequency is not limited to the generation of the plural frequencies. Therefore, in the modification, an example of the method of computing the eigenfrequency different from the embodiments will be described below.

In the modification, the frequency generated by the frequency generating unit is varied in the range including the frequency presumed to be the eigenfrequency. The frequency which is generated when the displacement measured by the strain gage 103 becomes the maximum is set at the eigenfrequency.

Figure 19:
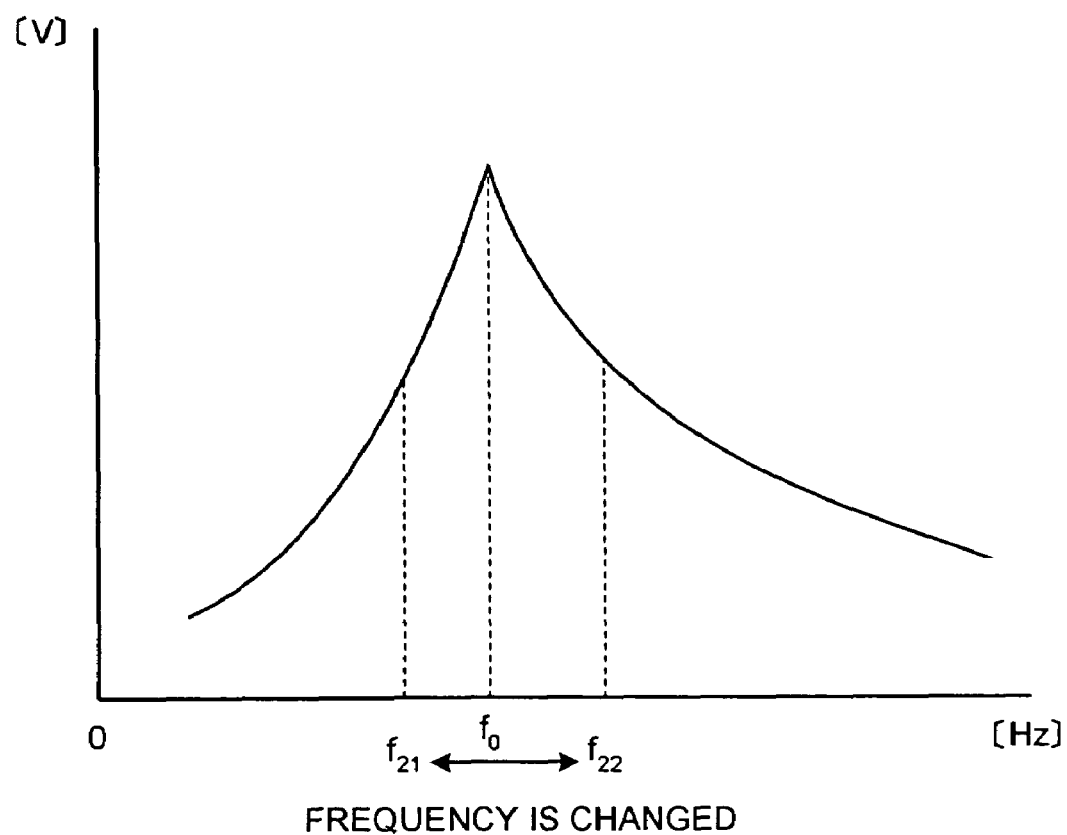
FIG. 19 is a graph in which a range of a frequency generated by a frequency generating unit of a concentration measuring apparatus according to a modification and the displacement measured in the range are shown on the transfer function.

FIG. 19 is a graph in which the range of the generated frequency and the displacement measured in the range are shown on the transfer function. In the modification, the frequency generating unit varies the frequency within the range of $f_{21}$ to $f_{22}$, and the voltage indicating the displacement at that point is inputted. Because the frequency can be specified when the displacement becomes the maximum, the frequency corresponding to the maximum displacement is set at the eigenfrequency.

The eigenfrequency can easily be computed by the modification without determining the transfer function.

In the above embodiments and modification, the vibration member is not limited to the elastic disc or the elastic plate. The vibration member may be formed in any shape. It is preferable that the vibration member has the shape increasing the flow distance of the fluid. For example, the vibration member may be formed in a spiral shape.

Figure 20:
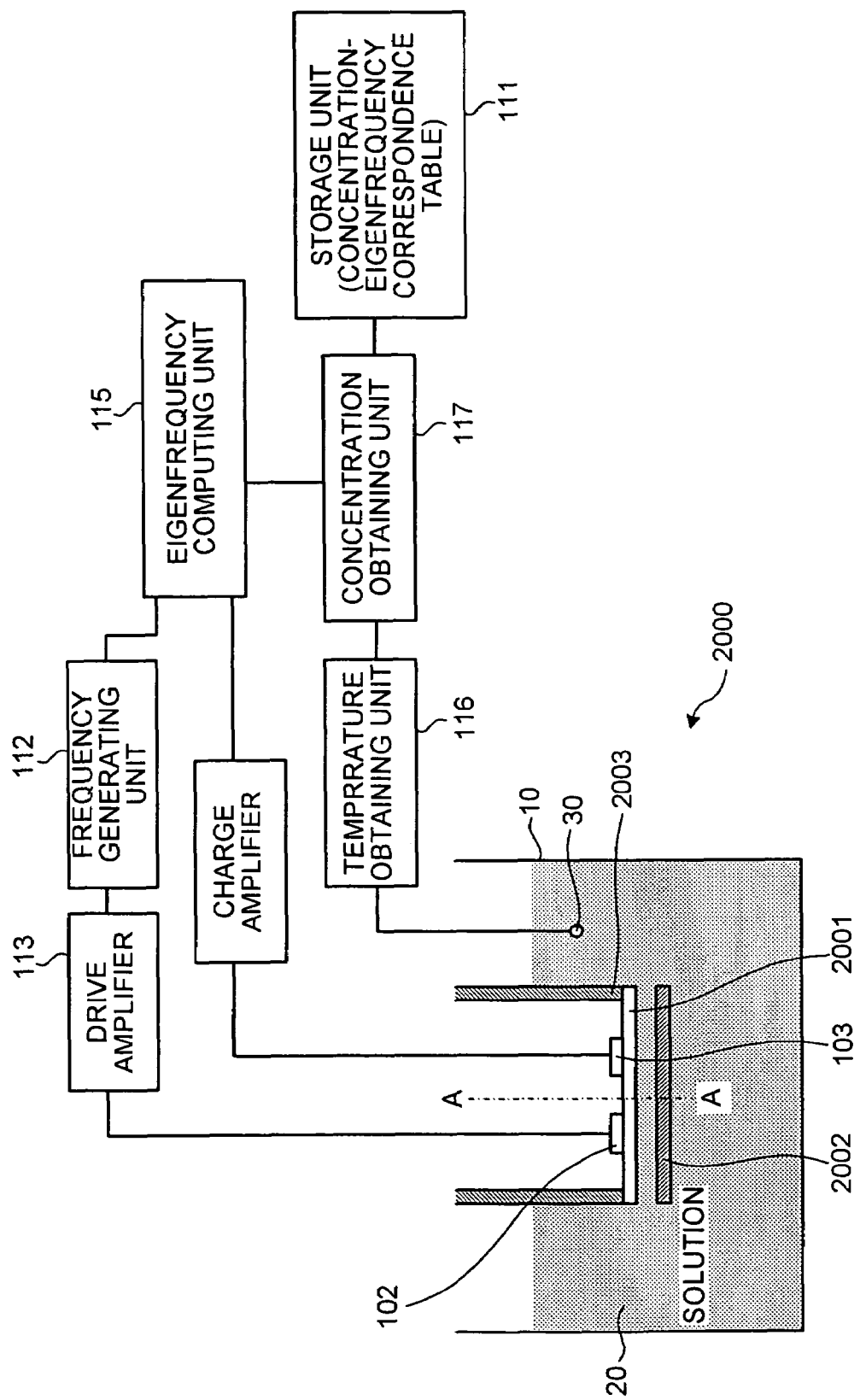
FIG. 20 is a block diagram showing a configuration of a concentration measuring apparatus according to another embodiment.
Figure 21:
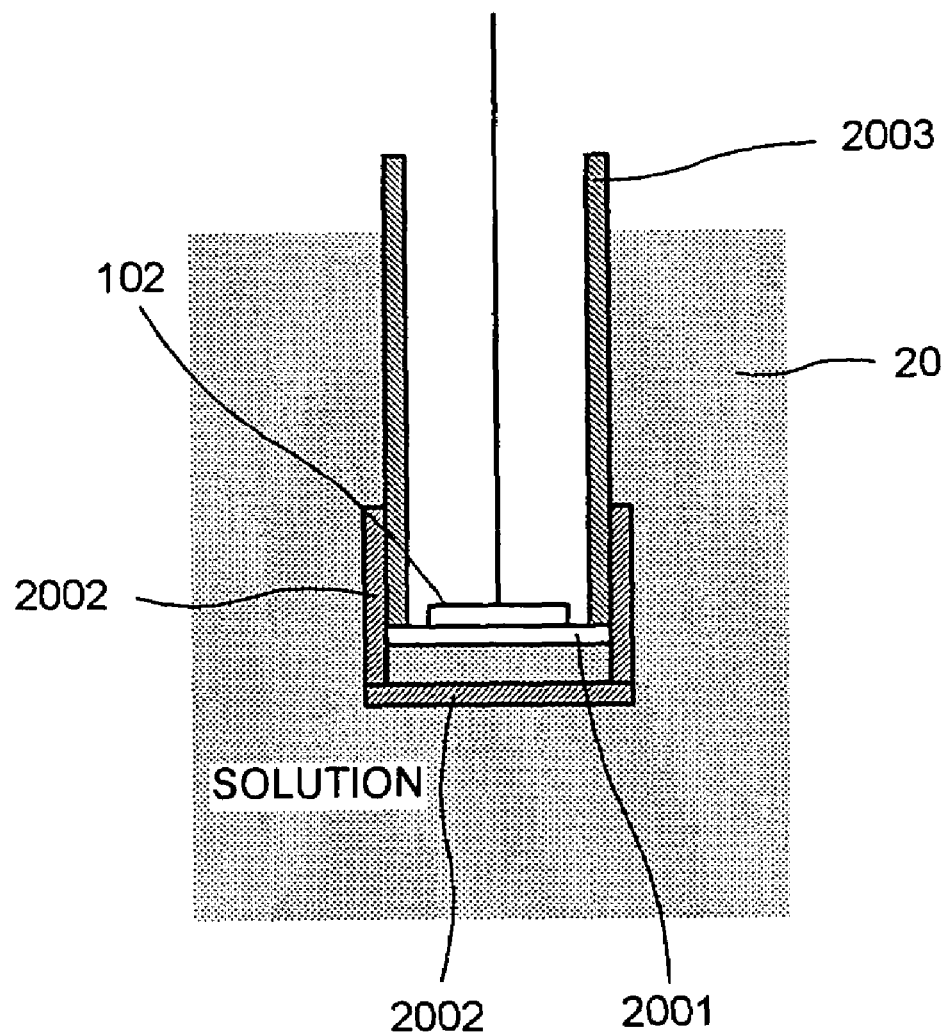
FIG. 21 is a sectional view taken along line A-A of FIG. 20.

In the above embodiments, the structure of the concentration measuring apparatus is not limited to the structure in which the whole of the vibration member is dipped in the mixed solution 20. Here, another embodiment will be described where only a part of the vibration member is dipped in the mixed solution 20. FIG. 20 is a block diagram showing a configuration of a concentration measuring apparatus according to another embodiment of the present invention. As shown in FIG. 20 of the embodiment, it is only necessary that one side surface of an elastic plate 2001 be in contact with the mixed solution 20. The concentration measuring apparatus 2000 includes a supporting member 2003; the elastic plate 2001 which is fixed to the supporting member 2003 and whose one side surface is in contact with the mixed solution 20; the vibration generating actuator 102 and the strain gage 103 which are provided on the other side surface of the elastic plate 2001; and a shielding plate 2002 which is provided on the opposed side and the side surface of the elastic plate 2001. FIG. 21 is a sectional view taken along line A-A of FIG. 20. As shown in FIG. 21, the shielding plate 2002 and the elastic plate 2001 form a cylindrical structure having a hollow extended in a longitudinal direction.

The cylindrical structure formed by the shielding plate 2002 and the elastic plate 2001 limits the fluid flow except for the longitudinal direction of the elastic plate 2001. With the fluid flow limited only to the longitudinal direction, vibrating the elastic plate 2001 allows obtaining the same advantages as obtained in the foregoing embodiment. Furthermore, in the embodiment shown in FIG. 20, since the vibration generating actuator 102 and the strain gage 103 do not need to be in contact with the fluid, it is not necessarily required to prevent the fluid from remaining on the vibration generating actuator 102, the strain gage 103, and their wiring or the like. Moreover, the vibration generating actuator 102 and the strain gage 103, which are provided on the other side surface of the elastic plate 2001, make a restriction on wiring or the like less.

Any mixed solution may be used as the mixed solution used in the above embodiments and modification. For example, it is thought that the mixed solution of water and alcohol is used. In the above embodiments, the nonviscous mixed solution is used as the fluid. However, in the case where the concentration of the viscous mixed solution is measured, the flow distance is also increased by measuring the concentration with the same configuration as the embodiments, so that the added mass effect can be generated to improve the accuracy.

In the above embodiments and modification, the temperature dependence can be decreased by obtaining the concentration from the eigenfrequency. Further, since the flowable area of the solution is limited by the shielding vessel or the like, the flow distance of the fluid is increased to improve the added mass effect. Therefore, the measuring accuracy of the concentration is improved.

As described above, the concentration measuring apparatus according to the above embodiments and modification is useful for the concentration measurement. Particularly, the concentration measuring apparatus according to the above embodiments and modification is suitable to the technology in which the temperature dependence of the solution is decreased by using the eigenfrequency in measuring the concentration.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A concentration measuring apparatus comprising:
a vibration member;
a shielding unit that limits a flowable area of a solution to be measured close to the vibration member;
a vibration control unit that vibrates the vibration member at a frequency;
a variation measuring unit that measures a physical variation of the vibration member vibrated;
an eigenfrequency computing unit that computes an eigenfrequency of the vibration member in the solution from the frequency and the variation; and
a concentration obtaining unit that obtains a concentration of the solution from the eigenfrequency and a correspondence between the eigenfrequency and the concentration of the solution.

2. The concentration measuring apparatus according to claim 1, wherein the vibration member is formed in a cuboid, a vibration generating unit is placed in the vibration member, and the vibration control unit vibrates the vibration member at the frequency using the vibration generating unit.

3. The concentration measuring apparatus according to claim 2, wherein the shielding unit has a cylindrical shielding vessel whose opening is provided in a longitudinal direction of the vibration member.

4. The concentration measuring apparatus according to claim 3, wherein, in the shielding unit, a length of the shielding vessel in a direction parallel to the longitudinal direction of the vibration member is formed longer than a minimum distance between an outer surface of the vibration member and the shielding vessel.

5. The concentration measuring apparatus according to claim 3, wherein, in the vibration member, a plurality of vibration generating units are placed at positions where a progressive wave generating a flow of the solution can be created, and the vibration control unit vibrates the plurality of vibration generating units with the frequency having a different phase which selectively excites the progressive wave.

6. The concentration measuring apparatus according to claim 1, wherein the vibration member is formed in a ring shape, the vibration generating unit is placed in the vibration member, and the vibration control unit vibrates the vibration member at the frequency using the vibration generating unit.

7. The concentration measuring apparatus according to claim 6, wherein, the shielding unit a first shielding member that limits flow of the solution in a radial direction of the ring-shaped vibration member and a second shielding member that limits flow of the solution toward an amplitude direction of the ring-shaped vibration member; the first shielding member is provided inside the ring-shaped vibration member and the second shielding member is provided outside the ring-shaped vibration member.

8. The concentration measuring apparatus according to claim 7, wherein, in the shielding unit, openings that become flow paths of the solution are provided in the first shielding member and the second sheilding member.

9. The concentration measuring apparatus according to claim 8, wherein, in the vibration member, a plurality of vibration generating units are placed at positions where a progressive wave generating a flow of the solution can be created, and the vibration control unit vibrates the plurality of vibration generating units with the frequency having a different phase which selectively excites the progressive wave.

10. The concentration measuring apparatus according to claim 1, further comprising a storage unit that stores information on the correspondence.

11. The concentration measuring apparatus according to claim 1, wherein the vibration control unit vibrates the vibration member at a plurality of different frequencies, and the eigenfrequency computing unit computes the eigenfrequency of the vibration member in the solution from the plurality of different frequencies and the variation during the vibration by each frequency.

12. The concentration measuring apparatus according to claim 1, wherein the vibration control unit vibrates the vibration member at a frequency in a range including the frequency presumed to be the eigenfrequency of the vibration member in the solution.

13. The concentration measuring apparatus according to claim 1, further comprising a temperature measuring unit that measures a solution temperature, wherein the concentration obtaining unit obtains the concentration of the solution from the eigenfrequency, the temperature, and a correspondence among the eigenfrequency, the temperature, and the concentration of the solution.

14. The concentration measuring apparatus according to claim 1, wherein the vibration control unit vibrates the vibration member at a frequency in which the vibration member becomes a vibration mode having an order number.

15. The concentration measuring apparatus according to claim 14, wherein the vibration control unit vibrates the vibration member at a frequency in which the vibration member becomes a primary vibration mode.

* * * * *